United States Patent [19]

Dessau

[11] Patent Number: 4,487,688

[45] Date of Patent: Dec. 11, 1984

[54] SELECTIVE SORPTION OF LUBRICANTS OF HIGH VISCOSITY INDEX

[75] Inventor: Ralph M. Dessau, Edison, N.J.

[73] Assignee: Mobil Oil Corporation, New York, N.Y.

[21] Appl. No.: 439,454

[22] Filed: Nov. 5, 1982

Related U.S. Application Data

[63] Continuation-in-part of Ser. No. 307,050, Sep. 30, 1981, abandoned, which is a continuation-in-part of Ser. No. 105,190, Dec. 19, 1979, Pat. No. 4,309,281.

[51] Int. Cl.$^3$ ............................................. C10G 25/03
[52] U.S. Cl. ............................... 208/310 Z; 585/820; 585/826
[58] Field of Search ................... 208/310 Z; 585/820, 585/826

[56] References Cited

U.S. PATENT DOCUMENTS

| | | | |
|---|---|---|---|
| 2,974,179 | 3/1961 | Fleck | 585/826 X |
| 2,982,715 | 5/1961 | Gibson | 208/310 Z |
| 3,053,913 | 9/1962 | Norris | 585/826 X |
| 3,258,417 | 6/1966 | Hess et al. | |
| 3,309,415 | 3/1967 | Young et al. | 585/826 X |
| 3,350,471 | 10/1967 | Mitchell | 585/826 X |
| 3,365,394 | 1/1968 | Cottle | 585/826 X |
| 3,663,430 | 5/1972 | Morris | 585/820 |
| 3,699,182 | 10/1972 | Cattanach | |
| 3,706,813 | 12/1972 | Neuzil | 208/310 Z X |
| 3,732,326 | 5/1973 | Chen | 208/310 Z X |
| 4,006,197 | 2/1977 | Bieser | 585/826 X |
| 4,059,505 | 11/1977 | Cartwright et al. | 585/826 X |
| 4,061,724 | 12/1977 | Grose et al. | 423/339 X |
| 4,069,142 | 1/1978 | Lauder et al. | 208/310 Z |
| 4,238,321 | 12/1980 | Florack | 585/826 X |
| 4,309,281 | 1/1982 | Dessau | 585/820 X |
| 4,367,364 | 1/1983 | Kulprathipanja et al. | 208/310 Z X |

Primary Examiner—Delbert E. Gantz
Assistant Examiner—Glenn A. Caldarola
Attorney, Agent, or Firm—A. J. McKillop; M. G. Gilman; L. G. Wise

[57] ABSTRACT

Lubricant components of high viscosity index are selectively separated from hydrocarbon base stocks by a selective sorption process using an intermediate pore size zeolite such as ZSM-5 as the sorbent. The process is of particular utility with synthetic lubricant stocks produced by the oligomerization of light olefins. The sorbed components may be desorbed from the zeolite to recover a high VI lubricant.

15 Claims, 1 Drawing Figure

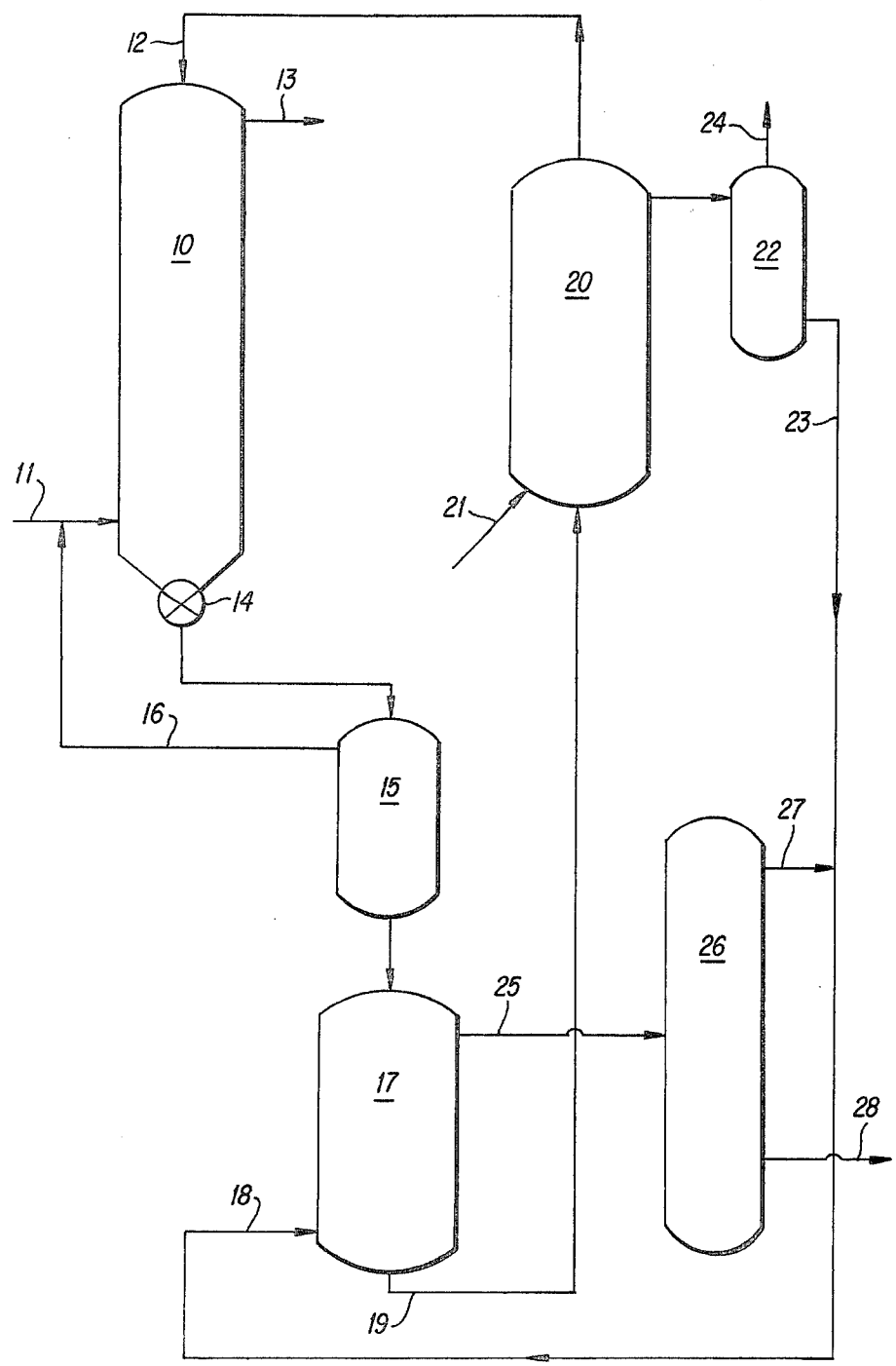

SELECTIVE SORPTION OF LUBRICANTS OF HIGH VISCOSITY INDEX

CROSS REFERENCE TO RELATED APPLICATIONS

This application is a continuation in part of U.S. application Ser. No. 307,050, filed Sept. 30, 1981, now abandoned, which in turn was a continuation in part of application Ser. No. 105,190, filed Dec. 19, 1979, now U.S. Pat. No. 4,309,281.

FIELD OF THE INVENTION

This invention relates to a process for making lubricants of high viscosity index and more particularly, to a process for making such lubricants by a selective sorption procedure using zeolitic sorbents.

BACKGROUND OF THE INVENTION

Viscosity index is an important characteristic of lubricants, especially hydrocarbon lubricants since it provides a measure of the extent to which the viscosity of the lubricant will vary with temperature. Normally, a high viscosity index, indicative of a relatively lower rate of change of viscosity with temperature, is desired in a lubricant because it will then be possible not only to predict the performance of the lubricant over a wider range of conditions but, in addition, the allowances which will have to be made for variations in lubricant properties will be smaller, so that the design characteristics of machinery can be optimized to a greater degree. It has long been known that the viscosity index (VI) of a hydrocarbon lubricant is related to its structure: paraffins have the highest viscosity indices and among the paraffins the more highly branched the paraffin is, the lower will be its viscosity index. For this reason, the more linear paraffinic lubricants have traditonally been preferred for their high viscosity index although the extent to which they may be employed in practical, commercial lubricants is limited by the fact that these same materials also tend to have high pour points, itself an undesirable feature. In practice, this has meant that a compromise must normally be found between the desirable attributes of high viscosity index and low pour point and generally the problem has found its practical solution in the use of dewaxed oils of paraffinic origin in which the linear and slightly branched paraffins have been removed by the dewaxing process but leaving sufficient of the slightly more highly branched paraffins to confer a high viscosity index without raising the pour point to unacceptable levels. Processes of this kind, however, require a base stock which possesses sufficient of the less highly branched paraffins but which is sufficiently free of the more highly branched paraffins, in order to confer the desired high viscosity index and low pour point. Base stocks of this kind may not always be available and some method must therefore be found for their manufacture. Such a method is provided by the present invention.

SUMMARY OF THE INVENTION

According to the present invention, hydrocarbon lubricants of high viscosity index are produced by selective sorption over a crystalline aluminosilicate zeolite of intermediate pore size such as ZSM-5, ZSM-11, ZSM-12, ZSM-23, ZSM-35, ZSM-38 or ZSM-48. The lubricant which is to be treated is contacted with the zeolite to sorb the components of high viscosity index selectively, leaving the low viscosity index components, which may then be removed. The high viscosity index components may then be desorbed from the zeolite by use of a solvent.

THE DRAWINGS

The single FIGURE of the accompanying drawings is a simplified schematic flowsheet illustrating a continuous sorption process for producing high VI lubricants.

DETAILED DESCRIPTION

The feed or starting material for the present process may comprise any hydrocarbon stock of suitable boiling point for use as a lubricant, which generally means that it will have an initial boiling point of at least 345° C. (about 650° F.). The end point may typically be as high as 650° C. (about 1200° F.) but may be lower, e.g. 540° C. (1000° F.). Boiling point is not, however, a basic characteristic of the feed which may be more readily described in terms of its viscosity characteristics and of the composition factors which confer these characteristics.

The feed will normally comprise a mixture of hydrocarbons of various kinds including aliphatic, aromatic and naphthenic (cycloaliphatic) constituents, depending upon its origin or method of manufacture. Because aromatic and naphthenic compounds generally make no substantial contribution to high viscosity indices, it is generally preferred that the content of these materials should be relatively low, so that the feed is relatively rich in paraffinic hydrocarbons. The slightly branched species which are to be sorbed should, however, have a critical molecular dimension of 6.8 A° or less in order that they may be sorbed.

Because the objective of the present process is to produce lubricating oils with high viscosity indices and low pour points, linear paraffins should be removed by a suitable dewaxing process. Dewaxing processes which will remove the linear paraffins are known and may be classified as solvent dewaxing processes or catalytic dewaxing processes. Solvent dewaxing processes employ a solvent such as a ketone, usually methyl ethyl ketone (MEK), either on its own or in combination with an aromatic solvent such as toluene to remove the wax by a chilling procedure which separates the waxy n-paraffins which are less soluble at lower temperatures. Processes of this kind are conventional. Catalytic dewaxing processes have become well known in recent years and are described, for example, in the Oil and Gas Journal Jan. 6, 1975, pages 69-73, U.S. Pat. Nos. Re. 28,398, 3,755,138, 3,956,102, 4,110,056, 4,176,050 and 4,222,855 to which reference is made for details of such processes. Catalytic dewaxing processes may be combined with other processing steps such as hydrodesulfurization or denitrogenation as described, for example, in U.S. Pat. Nos. 3,668,113 and 3,894,938, to which reference is made for details of such processes. After treatment for removal of waxy paraffins in this way, the paraffinic feed will consist essentially of paraffins with varying degrees of chain branching and with varying individual viscosity chracteristics; treatment by the present selective sorption process will resolve these constituents into a high viscosity index fraction, comprising the less highly branched compounds, and a low viscosity index fraction comprising the more highly branched compounds. The dewaxed feed, substantially free of linear paraffins (n-paraffins), will normally have a Pour Point (ASTM Test D-97) of less than −18° C. (0° F.) and frequently much lower, e.g. −40° C. (−40° F.), −50° C. (about −45° F.), −60° C. (about −50° F.). Because the high VI product from the present sorption process will have relatively less of the highly branched paraffins which contribute to low pour points, a slight elevation of pour point may be noted but because the linear n-paraffins have been removed completely or almost so by the preliminary dewaxing step, the product will still have a low Pour Point, generally not more than 5° C. or 10° C. (9° F.) above that of the feed, and in most cases still below −18° C. (0° F.).

The present process is particularly useful with synthetic lubricant stocks which consist essentially of linear and branched-chain hydrocarbons, with varying degrees of chain branching among the branched chain compounds. These synthetic materials are usually principally aliphatic; olefins may be present, depending upon the synthetic procedure used and any treatments subsequent to the initial synthesis. Generally, it is preferred to remove any olefins which are present and this may suitably be done by hydrogenation to the corresponding paraffins. A preferred type of feed for the present process comprises a synthetic lubricant base stock produced by the oligomerization of olefins. Stocks of this kind may be obtained by known processes and will normally have an initial boiling point of at least 345° C. (about 650° F.). Processes for producing lubricants by the oligomerization of olefins are known and may use olefins such as decene or dodecene, as described, for example, in U.S. Pat. Nos. 3,149,178 and 3,833,678, British Pat. No. 1,075,305, Ind. Eng. Chem. Prod. Res. Dev. 1980, 19, 2–6 and 15–19, to which reference is made for details of such processes. a preferred type of lubricant feedstock is provided, however, by the oligomerization of light, shorter chain ($C_6$-) olefins such as propylene and butylene, preferably with hydrogenation of the oligomer product to remove any residual unsaturation which would otherwise lead to instability in the lubricant product. The oligomerization process may be carried out over various catalysts including the Lewis acid type catalysts described in connection with the decene and dodecene oligomerization processes mentioned above but the preferred oligomerization catalysts are the crystalline aluminosilicate zeolites which have a silica:alumina ratio of at least 12:1 and a Constraint Index of 1 to 12. These zeolites are described n detail below. The preferred zeolites for the purposes of oligomerizing the olefins are ZSM-5 and ZSM-12 and for this purpose, the zeolites preferably have a silica:alumina ratio of at least 30:1 and preferably even higher, e.g. 70:1, 100:1, 200:1 or more. The olefin is generally contacted with the zeolite catalyst at a temperature of at least 150° C., preferably at least 200° C. and normally in the range of 200° C. to 300° C., at space velocities of 0.1–10 WHSV, usually 0.5–5 WHSV. Processes of this kind are described in detail in U.S. Pat. Nos. 4,227,992 and 4,254,295 to which reference is made for further details of such processes.

The lubricant base stocks produced by the zeolite catalyzed oligomerization of light olefins are generally chracterized by a high viscosity index, generally above 80 and in favorable cases above 90. The pour points of these lubricants are generally very low, usually below −40° C. and often lower, e.g. −50° C. After treatment by the present selective sorption process the viscosity index will usually rise to at least 80 and in favorable cases to over 100 or even higher. Viscosity indices of 110 or even 115 have been obtained in this way.

The lubricant base stock is subjected to the selective sorption of the high viscosity index components over a crystalline aluminosilicate zeolite of certain characteristics. Zeolites of this kind comprise a three dimensional lattice of $SiO_4$ tetrahedra crosslinked by the sharing of oxygen atoms and which may optionally contain other atoms in the lattice, especially aluminum in the form of $AlO_4$ tetrahedra; the zeolite will also include a sufficient cationic complement to balance the negative charge on the lattice. Zeolites have a porous crystal structure which is capable of regulating the access to an egress from the intracrystalline free space. This control, which is effected by the crystal structure itself, is dependent both upon the molecular configuration of the material which is or, alternatively, is not, to have access to the internal structure of the zeolite and also upon the structure of the zeolite itself. The pores of the zeolite are bounded by rings which are formed by the regular disposition of the tetrahedra making up the anionic framework of the crystalline aluminosilicate, the oxygen atoms themselves being bonded to the silicon or aluminum atoms at the centers of the tetrahedra. A convenient measure of the extent to which a zeolite provides this control for molecules of varying sizes to its internal structure is provided by the Constraint Index of the zeolite: zeolites which provide but highly restricted access to and egress from the internal structure have a high value for the Constraint Index and zeolites of this kind usually have pores of small size. Contrariwise, zeolites which provide relatively free access to the internal zeolite structure have a low value for the Constraint Index. The method by which Constraint Index is determined is described fully in U.S. Pat. No. 4,309,281 and J. Catalysis 67, 218–222 (1981) to which reference is made for details of the method together with examples of Constraint Index for some typical zeolites. Because Constraint Index is related to the crystalline structure of the zeolite but is nevertheless determined by means of a test which exploits the capacity of the zeolite to engage in a cracking reaction, that is, a reaction dependent upon the possession of acidic sites and functionality in the zeolite, the sample of zeolite used in the test should be representative of zeolitic structure whose Constraint Index is to be determined and should also possess requisite acidic functionality for the test. Acidic functionality may, of course, by varied by conventional artifices including base exchange, steaming or control of silica:alumina ratio.

The silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of $Al_2O_3$ or cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. The disparities are particularly troublesome when certain treatments such as dealuminization methods which result in the presence of ionic aluminum free of the zeolite structure are employed. Due care should therefore be taken to ensure that the framework silica:alumina ratio is correctly determined.

The zeolites used in the present selective sorption process have a Constraint Index of 1 to 12 and a silica:alumina ratio of at least 12 and because the hydrophobic characteristics, i.e. the affinity for hydrocarbons, are related to the silica:alumina ratio, it is preferred that the zeolites with higher silica:alumina ratios should be used. The silica:alumina ratio will frequently be at least 30:1 but higher ratios, e.g. 70:1, and higher, particularly the ratios above 500:1, e.g. 1600:1, may also be used; the silica:alumina ratio of these materials may, in fact, go to infinity.

Specific zeolites conforming to the prescribed values of Constraint Index and silica-alumina ratio include ZSM-5, ZSM-11, ZSM-12, ZSM-23, ZSM-35, ZSM-38, the ZSM-5/ZSM-11 intermediate and ZSM-48 which are disclosed, respectively, in U.S. Pat. Nos. 3,702,886; 3,709,769; 3,832,449; 4,076,842; 4,016,245, 4,046,859 and 4,229,424 and European Patent Publication No. 15132. Highly siliceous forms of ZSM-5 are disclosed in U.S. Pat. No. Re. 29,948, of ZSM-11 in European Patent No. 14059 and of ZSM-12 in European Pat. No. 13630. Reference is made to these patents for complete details of these zeolites and the preparation. Of them, ZSM-5 is preferred.

As mentioned above, the silica:alumina ratio of the zeolites may be as high as infinity, indicating that the so-called zeolite is a polymorph of silica, conceivably with lattice defects. It is also possible that metals other than aluminum may be present at tetrahedral sites within the lattice; trivalent metals such as boron, chromium, iron, gallium or lanthanum are particularly suitable in this respect and materials of this type may be used in the present process.

When the zeolites have been prepared in the presence of organic cations, they are catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite; but it does appear to favor the formation of this special type of zeolite.

When synthesized in the alkali metal form, the zeolite is conveniently converted to the hydrogen form, generally by intermediate formation of the ammonium form as a result of ammonium ion exchange and calcination of the ammonium form to yield the hydrogen form.

The sorption selectivity of the zeolite can be improved by reducing the diffusional rate characteristics of the zeolite. The diffusional rate characteristic is defined as the rate of which a zeolite, or other adsorbent, sorbs a particular hydrocarbon, e.g. hexane or o-xylene. Modification of the diffusional rate characteristics suitably may be effected by precoking. Another way of achieving desired lower diffusional rate characteristics is the use of large crystal size zeolite having a minimum crystal dimension greater than about 0.5 micron. Generally, the crystal size should be in the approximate range of from 0.5 to greater than 250 microns, and preferably in the range of 0.5 to 250 microns.

Yet, another way of achieving desired lower diffusional rate characteristics is to incorporate, such as by cation exchange, bulky cations such as cesium or tetramethylammonium cations within the zeolite. Other cations which may be exchanged into the zeolite to confer a lower diffusional rate and thereby increase selectivity include $Na^+$, $H^+$, $Cu^{++}$, $K^+$, $Sr^{++}$ and similar cations. The sorption selectivity of the exchanged zeolite may be correlated with the ionic radius of the cation involved The silica:alumina ratio has also been found to have an effect upon the sorption selectivity of the zeolites. For example, HZSM-5 having a silica-alumina ratio of 1670:1 may have a greater selectivity from four to five times that of HZSM-5 having a silica:alumina ratio of 75:1 depending upon the identity of the species with which it comes into contact. Similarly, it has also been found that steaming the zeolite may increase its selectivity. For example, the unsteamed HZSM-5 may have a selectivity factor of 3.2 but after steaming for 2 hours at 540° C., the selectivity factor may increase to 7.3, again depending upon the identity of the species in contact with the zeolite.

The sorption process may be carried out in the presence or absence of a solvent or it may even be carried out in the gas phase although this will normally not be preferred. If a solvent is used in liquid phase operation, it should have a critical molecular dimension of at least 6.8 A° in order to prevent it from competing with the species which are intended to be sorbed on the zeolite. Suitable solvents of this kind include, for example, 1,3,5-trimethylbenzene (mesitylene), 1,3,5-triisopropyl benzene, tetramethylsilane and 1,3-di(trifluoromethyl)benzene. The process may be conducted in the presence of polar compounds e.g. water, alcohol or aqueous solutions.

The temperature at which the sorption process is conducted is not critical as long as it is maintained below that required for chemical reaction to occur, e.g. below cracking temperature. The temperature should thus be maintained below about 100° C. when an acidic zeolite is used (e.g. having a Alpha value greater than 10). A method for determing Alpha is described in U.S. Pat. No. 4,0162,218 and J. Catalysis VI, 278–287, 1966 to which reference is made for details of the method. When a relatively non-acidic zeolite is used, e.g. one having a $SiO_2/Al_2O_3$ mole ratio of about 1000:1 or more, or when the zeolite has been converted to the alkalimetal-containing form, e.g. Na, by ion-exchange, for instance, higher temperatures may be used, such as up to about 400° C. Preferably, the process is conducted in the temperature range between ambient and about 150° C.

The components of the feed which have become sorbed on the zeolite may be recovered by conventional desorption techniques such as steam stripping or solvent extraction. The process may be carried out in a batch operation or in a continuous (flow type) sequence, e.g. a continuous chromatographic type operation. A form of a continuous sorption process is illustrated in the simplified flowsheet shown in the Figure.

In the flowsheet, the feed comprising a dewaxed lube stock or a synthetic lube stock produced by olefin oligomerization is fed into a sorption tower 10 through inlet 11 in which it contacts the zeolitic sorbent, preferably ZSM-5. The zeolite enters the sorption tower at the top by way of sorbent inlet 12 and then passes downwardly through the tower in countercurrent to the upwardly flowing lube so that the desired selective sorption takes place. The treated effluent which leaves the tower by way of outlet 13 comprises the low V.I. components of the feed which have not been sorbed by the zeolite. The zeolite, containing the sorbed, high V.I. components accummulates as a moving bed at the foot of the tower from which it is removed through outlet 14. The slurry of oil and zeolite then passes to decanter 15 where a separation of the occluded oil and the zeolite takes place, with the oil being returned to inlet 11 through conduit 16. The zeolite then passes to solvent extraction tower 17 in which the sorbed components of the feed are recovered by the use of a solvent such as benzene, toluene, hexane or another suitable hydrocarbon. The solvent enters the extraction tower through solvent inlet 18 and passes upwardly through the tower in countercurrent to the descending zeolite which is withdrawn through outlet 19 at the bottom after the sorbed components of the feed have been removed by the solvent. The zeolite, now containing sorbed solvent, passes to solvent stripper 20 where the solvent is removed by hot air, steam or other suitable means, suitably introduced through inlet 21. The stripped zeolite then passes back to sorption tower 10 by way of inlet 12. The gases from the solvent stripper are treated in solvent recovery system 22 and the solvent recycled by way of conduit 23, with gases leaving through exhaust 24.

The solution of the sorbed feed components in the solvent leaves extraction tower 17 through outlet 25 and passes to solvent separator 26 in which the lube components are separated from the solvent by fractionation. The separated solvent is then recycled by way of conduit 27 and the desired, high V.I. lube recovered at outlet 28.

The invention is illustrated by the Examples given below in which all parts, percentages and proportions are expressed by weight, unless the contrary is stated. In these Examples, the degree of chain branching has been used as a measure of the viscosity index of the lubricant since it has been found that there is a reasonable inverse correlation between viscosity index and the degree of chain branching in paraffinic hydrocarbon lubricants. In order to provide a numerical measurement of the degree of chain branching, the ratio $R^*$ of methylene to methyl protons in the various fractions is used. This ratio is determined by simple measurement of the NMR peak heights of the methylene and methyl protons, respectively. The higher the value of $R^*$, the more linear (less branched) is the molecule and hence its viscosity index. Other methods of measuring the degree of chain branching may, of course, be used to establish a correlation with viscosity index.

EXAMPLES 1-3

A 345° C.+ lubricant produced by the oligomerization of a mixture of propylene and butylene over an HZSM-5 catalyst at elevated pressure and having a V.I. of 82 was subjected to selective sorption by ZSM-5 type zeolite solvents using bulky solvents such as tetramethylsilane (TMS) and mesitylene (1,3,5-trimethylbenzene). The sorptions were carried out at room temperature with the TMS solvent and at 162° C. under reflux with the mesitylene. The sorbed fractions were recovered from the zeolite by desorption with n-hexane by continuous extraction in a Soxhlet type apparatus. The $R^*$ values of the sorbed and non-sorbed fractions were determined by measuring the NMR peak heights for the methylene and methyl protons of the respective fractions.

$$R^* = \frac{\text{Methylene proton } NMR \text{ peak height}}{\text{Methyl proton } NMR \text{ peak height}}$$

The viscosity indices were determined by measurement of the kinematic viscosities at 40° C. and 100° C. according to ASTM D-2270.

The ZSM-5 zeolites used both had silica:alumina ratios of approximately 70:1. The zeolite identified as ZSM-5A has a crystal size of 0.1 microns; the zeolite identified as NH$_4$ ZSM-5-B was a small crystal ZSM-5 (crystal size less than 0.05 microns) in the NH$_4$ form with an alumina binder (35 percent binder). The test conditions used together with the results obtained are given in Table 1 below.

TABLE 1

| | | Lubricant Sorption | | R* | |
|---|---|---|---|---|---|
| Ex. | Lube Amt., g. | Sorbent | Solvent | Sorbed | Non-Sorbed |
| 1 | 10 | ZSM-5-A 50 g | TMS 94 g | 3.79 | 1.57 |
| 2 | 10 | NH$_4$ZSM5-B 77 g | TMS 100 g | 2.70 | 1.61 |
| 3 | 8 | NH$_4$ZSM5-B 77 g | mesitylene 100 g | 2.61 | 1.67 |

EXAMPLE 4

The procedure of Examples 1-3 was repeated with a different 345° C.+ lubricant fraction produced by the ZSM-5 catalyzed oligomerization of propylene and butylene at elevated pressure. This fraction had a V.I. of 93. The zeolite sorbent used was the same as in Examples 2 and 3.

The results are given in Table 2 below.

TABLE 2

| | | Lubricant Sorption | | | |
|---|---|---|---|---|---|
| Ex. | Lube Amt., g. | Sorbent | Solvent | Sorbed | Non-Sorbed |
| 4 | 10 | NH$_4$ZSM-5-B 75 g | TMS 100 g | 2.21 | 1.57 |

The results in Examples 1-4 are above clearly indicated that the sorbed fraction is significantly less branched than the non-sorbed fraction. Since the degree of chain branching is related to the viscosity index of the product, the sorbed fraction will be of higher viscosity index.

EXAMPLES 5-7

A different 345° C.+ lubricant fraction produced in a similar manner to those of Example 1-4 but having a viscosity index of 105, was subjected to selective sorption over an HZSM-5-B extrudate (zeolite silica:alumina ratio of 70:1, crystal size under 0.05 microns, 35 percent alumina binder). The sorption was carried out in the presence of TMS solvent at room temperature.

The results are shown in Table 3 below.

TABLE 3

| Fraction | Lubricant Sorption | | R* |
|---|---|---|---|
| | Wt (g) | Percent | |
| Example 5 | | | |
| 40 g lube:148 g sorbent:100 g TMS | | | |
| Non-Sorbed | 22.37 | 56.0 | 2.02 |
| Sorbed No. 1 | 9.09 | 22.7 | 2.40 |
| Sorbed No. 2 | 7.89 | 19.7 | 2.61 |
| Sorbed No. 3 | 0.01 | — | 6.88 |
| Total Recovery | | 98.4 | |
| Example 6 | | | |

TABLE 3-continued

| | Lubricant Sorption | | |
|---|---|---|---|
| Fraction | Wt (g) | Percent | R* |
| 35 g lube:129 g sorbent:100 g TMS | | | |
| Non Sorbed | 22.17 | 63.3 | 1.95 |
| Sorbed No. 1 | 12.62 | 36.1 | 2.41 |
| Sorbed No. 2 | 0.08 | 0.2 | |
| Total Recovery | | 99.6 | |
| Examples 7 | | | |
| 50 g lube:200 g sorbent:50 g TMS | | | |
| Non-Sorbed | 30.23 | 60.4 | 2.03 |
| Sorbed | 18.43 | 36.9 | 2.48 |
| Total Recovery | | 97.3 | |

The kinematic viscosities of the sorbed and non-sorbed fractions of Examples 6 and 7 were determined at 40° C. and 100° C. and from these the viscosity indices of the fractions determined. The results are set out in Table 4 below.

TABLE 4

| | Viscosity Properties | | |
|---|---|---|---|
| Fraction | KV at 40° C., cSt | KV at 100° C., cSt | VI |
| Ex. 6 Sorbed | 24.16 | 4.720 | 114.5 |
| Ex. 6 Non-Sorbed | 26.45 | 4.775 | 98.9 |
| Ex. 7 Sorbed | 24.54 | 4.820 | 117.3 |
| Ex. 7 Non-Sorbed | 26.72 | 4.800 | 100.3 |
| Original lube | 26.27 | 4.837 | 105.1 |

The results given above show that the viscosity index of the oils correlates with the degree of chain branching, represented here by the R* values, also that the sorbed fractions have higher VI values than the non-sorbed fractions of the original lubricant.

I claim:

1. A process for the selective separation of hydrocarbon lubricant fractions of high viscosity index from a hydrocarbon lubricant base stock, below cracking temperature which comprises contacting the base stock with a crystalline zeolite having a silica:alumina ratio of at least 12:1 and a Constraint Index of 1 to 12, to sorb the high viscosity index fractions of the zeolite.

2. A process according to claim 1 in which the zeolite has a silica:alumina ratio greater than 70:1.

3. A process according to claim 1 in which the zeolite has a silica:alumina ratio greater than 500:1.

4. A process according to claim 1 in which the zeolite is ZSM-5, ZSM-11, ZSM-12, ZSM-23, ZSM-35 or ZSM-38.

5. A process according to claim 1 in which the zeolite is ZSM-5 or ZSM-11.

6. A process according to claim 5 in which the zeolite has a crystal size greater than 0.5 microns.

7. A process according to claim 1 in which the lubricant base stock comprises a dewaxed base stock.

8. A process according to claim 1 in which the lubricant base stock comprises a synthetic base stock produced by the oligomerizatiion of olefins.

9. A process according to claim 8 in which the synthetic base stock is produced by the oligomerization of light olefins over a catalyst comprising a zeolite having a silica:alumina ratio of at least 12:1 and a Constraint Index of 1 to 12.

10. A process according to claim 1 in which the lubricant base stock has a viscosity index of at least 10 less than that of the sorbed fractions.

11. A process according to claim 1 which includes the step of recovering the sorbed fractions from the zeolite.

12. A process according to claim 11 in which the sorbed fractions are recovered from the zeolite by solvent extraction.

13. A process for selective separation of hydrocarbon lubricant oil fractions from a dewaxed hydrocarbon mixture rich in paraffinic hydrocarbons having a critical molecular dimension of 6.8 Å or less comprising
   contacting the mixture is liquid phase with a crystalline zeolite of intermediate pore size having a constraint index of 1 to 12 at a temperature below about 100° C. to sorb a high viscosity index paraffinic lubricating oil fraction selectively on the zeolite, and
   recovering the sorbed high viscosity index fraction.

14. The process of claim 13 wherein the sorbed fraction is recovered by solvent extraction of high viscosity index paraffinic sorbate from zeolite sorbent.

15. The process of claim 13 wherein the sorbed fraction has a viscosity index at least 10 higher than the dewaxed mixture.

* * * * *

UNITED STATES PATENT AND TRADEMARK OFFICE
CERTIFICATE OF CORRECTION

PATENT NO. : 4,487,688

DATED : December 11, 1984

INVENTOR(S) : Ralph M. Dessau

It is certified that error appears in the above-identified patent and that said Letters Patent is hereby corrected as shown below:

Col. 3, line 49, "n" should read —in—.

Col. 8, line 36, add the heading "R*" above Sorbed & Non-Sorbed columns in Table.

Col. 9, line 32, "oilscorrelates" should read —oils correlates—.

Col. 10, line 14, claim 8, "oligomerizatiion" should be —oligomerization—.

Col. 10, line 32, claim 16, "mixture is liquid" should be —mixture in liquid—.

Signed and Sealed this

Sixth Day of August 1985

[SEAL]

Attest:

DONALD J. QUIGG

Attesting Officer

Acting Commissioner of Patents and Trademarks